United States Patent [19]

Steigmeier et al.

[11] 4,314,763
[45] Feb. 9, 1982

[54] DEFECT DETECTION SYSTEM

[75] Inventors: Edgar F. Steigmeier, Hedingen; Karl Knop, Zurich, both of Switzerland

[73] Assignee: RCA Corporation, New York, N.Y.

[21] Appl. No.: 813

[22] Filed: Jan. 4, 1979

[51] Int. Cl.³ ............................................. G01N 21/88
[52] U.S. Cl. .................................. 356/237; 250/224; 356/342
[58] Field of Search ............... 356/237, 240, 342, 445, 356/446–448, 337, 338; 350/6.3; 250/572, 224, 203 CT; 358/342; 343/5 SC

[56] References Cited

U.S. PATENT DOCUMENTS

| | | | |
|---|---|---|---|
| 2,913,568 | 11/1959 | Kates | 250/225 |
| 3,176,306 | 3/1965 | Burns | 250/572 X |
| 3,229,564 | 1/1966 | Meltzer | 356/448 X |
| 3,561,876 | 2/1971 | Hoffman | 356/351 |
| 3,565,568 | 2/1971 | Hock | 356/369 |
| 4,002,827 | 1/1977 | Nevin et al. | 358/140 |
| 4,128,834 | 12/1978 | Katagi | 343/5 SC X |

OTHER PUBLICATIONS

Conference on Laser and Electrooptical Systems, 7–9, Feb. 1978, OSA/IEE San Diego, Calif., pp. 90, 91, 92.
Electronics, Mar. 16, 1978 pp. 48, 50.
Patrick, W. J. and Patzner, E. J., "The Detection of Surface Defects on Silicon Wafers by Scattered Light Measurements," Semi-conductor, Silicon 1973.

Primary Examiner—John K. Corbin
Assistant Examiner—Bruce Y. Arnold
Attorney, Agent, or Firm—Samuel Cohen; H. Christoffersen; William Squire

[57] ABSTRACT

A laser beam projected through a prism in a direction normal to the surface of a circular wafer is focused into a spot area and scanned along a spiral path on this surface. The focusing means comprises a relatively large aperture lens and the prism is on the lens axis. The retroreflected specular light passes through the lens and is prevented from reaching a light detector in the image plane of the lens by the prism. When the beam illuminates a microscopic surface defect on the wafer, the light is diffracted and reflected therefrom, and the lens captures that portion of the reflected light within the solid angle subtended by the lens, and passes that portion thereof not blocked by the prism, to the light detector. The output of the detector may be employed to intensity modulate the beam of a cathode-ray tube display, the beam of which is spirally scanned in synchronism with the scanning of the light beam.

13 Claims, 6 Drawing Figures

DEFECT DETECTION SYSTEM

The present invention relates to an improved system for optically detecting microscopic defects in a specularly reflecting surface of a given object and, more particulary, to such a system which is capable of deriving an image display of the spatial distribution of the locations of detected microscopic defects on the surface.

Silicon wafers, which are circular thin planar disks, are widely used in the manufacture of semi-conductor devices such as integrated circuits and the like. The slightest defects in the surface, such as dust particles too small to be seen with the naked eye, fingerprints, manufacturing defects, and the like, are undesirable and should be detected as soon as possible in the manufacturing process to reduce costs.

Some presently available scan devices do not produce a display of such a defect pattern. Other systems that do produce such a display use rectangular scanning systems in which the beam is scanned along x-y rectangular coordinates. This is not suitable for circular objects. The edges of the objects are intercepted by the scan beam and produce transient signals which interfere with the efficient operation of the instrument.

Other systems collect a relatively small portion of diffracted light scattered from a microscopic defect and, therefore, have less than optimum sensitivity. An example of such a system is described in more detail in an article entitled, The Detection of Surface Defects on Silicon Wafers by Scattered Light Measurements by W. J. Patrick and E. J. Patzner, Semi-Conductor, Silicon 1973, the Electro-Chemical Society, Inc., Princeton, N.J., 1973, pages 482-490. Other light scattering scanning devices are described in articles by D. R. Oswald and D. F. Monroe, Journal of Electronic Materials 3, 225 (1974) and H. J. Ruiz, C. S. Williams and F. A. Padovani, Journal of Electro-Chemical Society 121, 689 (1974).

The system of the present invention, in contrast to those of the prior art, collects a large portion of all the diffracted light scattered from a microscopic defect in the specularly reflecting surface of an object. More specifically, in accordance with the principles of the present invention, the surface is scanned with an incident beam of light directed substantially normally to the surface, which beam illuminates a spot area of the surface which is small relative to the entire area of the surface, but is large relative to the area of a microscopic defect. Focusing means having a large aperture area relative to the spot area captures substantially all reflected light within the solid angle subtended by the focusing means. A photo detector located in an image plane of the focusing means receives light reflected by the surface. A spatial filter having a small cross-section relative to that of the lens removes that portion of the reflected light which is specularly reflected.

Figure 1:
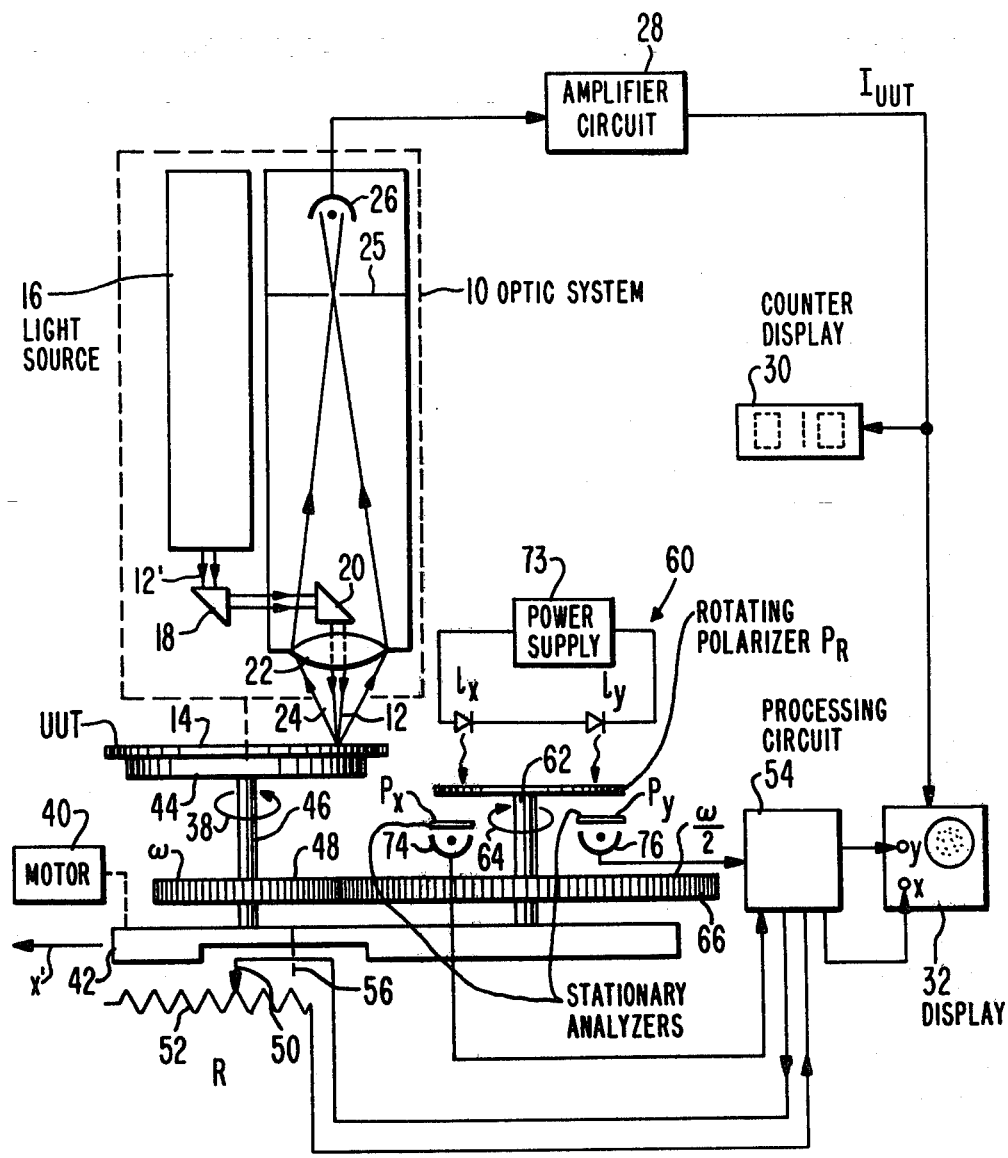
FIG. 1 is a side-elevational, partially block diagrammatic view of a system embodying the present invention.

In FIG. 1, system 10 includes a light source 16 which projects beam 12' through a series of prisms 18 and 20 and then through focusing means such as lens 22. The term light herein includes infrared, visible and ultraviolet light. Light source 16 may be a low-power (such as 1 millivolt) laser, for example a He-Ne laser producing light of 6328 angstroms wavelength which is focused by lens 22 into a spot 250 micrometers in diameter at 12. This relatively small spot provides high resolution to the system. The beam 12 of laser light produced by lens 22 is projected onto the surface 14 of the unit under test (UUT), which may be a circular wafer of silicon as used in the manufacture of integrated circuits and other semiconductor devices. The position of the light source 16 is not critical to the invention, but the position of the beam 12 between the prism 20 and the surface 14 is important. The axis of beam 12 should be perpendicular to the surface 14.

The surface 14 of an acceptable wafer should be smooth and plane. By surface is meant both the exposed surface and the underlying material to the depth at which the light may penetrate. In this case, the specular light that is reflected from the planar surface 14 follows the path of beam 12, that is, it is retroreflected toward prism 20. Prism 20 acts as a spatial filter for the specularly retroreflected light along the axis of beam 12. Thus, any light retroreflected from an acceptable surface, i.e. one that is normal to the axis of the beam 12, is incident on prism 20 and is not passed into detector 26. The prism 20 is larger than beam 12 and, for example, may have sides which are $\frac{1}{4}''$ by $\frac{1}{4}''$.

Should the position of the surface 14 being scanned have a defect therein, such as caused by dust particles, foreign matter, fingerprints, nicks, internal defects or the like which include those which are microscopic in size having submicrometer dimensions, then such variations in the surface will reflect and diffract the incident beam 12 into a substantially broader pattern 24. The broader pattern 24 is co-axial with the beam 12 in the sense it may be dispersed 360° around the axis of beam 12, and the lens 22 collects a significant portion of this broader pattern. This broader pattern provides improved sensitivity to the present system. Lens 22 focuses the broader pattern 24 onto a high speed photodiode detector 26 which is on the extension of the center axis of beam 12. The lens 22 may be f2 and 1 inch in diameter. The defects may be as small as about 1 micrometer spheres or if linear have an area approximately equivalent to approximately a 1 micrometer diameter. A linear defect may extend a distance beyond the 250 micrometer diameter in which case its shape will be detected by the display. In any case, even though it is 1 micrometer or smaller, the defect diffracts a sufficient amount of light beyond prism 22 so as to be detected by detector and with high signal to background ratio in that the retroreflected specular light is filtered by prism 20. Thus in the present embodiment a photodiode may be used as compared to photomultipliers in the prior art systems. The apertured mask 25 acts as a second spatial filter at system 10 and it prevents ambient light from being projected onto the detector 26. The output of detector 26 is applied to an amplifier circuit 28 which applies the amplified detected signal both to the counter display 30 and the cathode-ray tube display 32.

The counter display 30 is a digital device for counting the number of defects detected. This is an optional feature and may be used for statistical and other purposes. The display 32 shows the relative spatial distributions of the locations of the defects and/or surface variations present on the UUT 14. The display may be a two dimensional display and if so will employ a form of scan such that the electron beam will be intensity modulated by a signal indicative of a defect at the time that it is in a position corresponding to that of the defect on the surface 14. Preferably the amplifier 28 is along in nature and produces an output at a level proportional to the input it receives from detector 26. This results in grey scale in the display, the intensity of the indications of defects on the display screen often being indicative of the forms of the defects. In the particular example illustrated herein, the beam 12 scans the UUT in spiral fashion and the electron beam of the display 32 is also scanned in spiral fashion in synchronism with the scanning of the UUT.

The unit under test (UUT) may be a circular disc whose surface it is desired to inspect. For this purpose the beam 12 may be scanned over the surface 14 in a spiral pattern 34 as is best illustrated by the dashed line in FIG. 3. This spiral scan provides an improved signal-to-noise ratio as compared with raster scan which may exhibit undesirable edge transient signals and flyback noise. The spot 36 of light is produced by the beam 12. The scanning is achieved by causing the spot 36 to move in the direction x' preferably at a constant speed while rotating the UUT in direction 38 at an angular preferably uniform speed ω. The movement of the spot 36 is achieved by holding the beam 12 in fixed position while driving the support 42 for the UUT 42 in the x' direction by a motor 40. In the alternative, beam 12 may be caused to traverse a spiral path and the UUT kept stationary.

The UUT is mounted to rotatable table 44 by means of a vacuum or by using some other conventional mounting arrangement. Table 44 is secured to a shaft 46 rotatably mounted on table 42. A gear 48 connected to a drive system (not shown) rotates the support 44 in the direction 38. A wiper arm 50 is connected (dashed line 56) to the table 42 and moves with the table 42 as the table translates in the direction x'. The wiper arm 50 is part of a potentiometer 52 which is connected to processing circuit 54.

Translation of the table 42 in the direction x' imparts a linear displacement to the spot 36 in the direction x' with respect to surface 14 of the UUT. The combination of the rotation of the UUT and linear displacements in the direction x' provides the spiral path 34 to the spot 36. The start of the path may be at the axis of rotation of the shaft 46, indicated at 34' in FIG. 3.

The coordinate transformation system 60 of FIG. 1 transforms the polar coordinates of the spot 36 on the surface 14 into suitable rectangular coordinate signals which are applied as x and y, horizontal and vertical respectively, coordinate inputs for the display produced by cathode-ray tube display 32.

Figure 4:
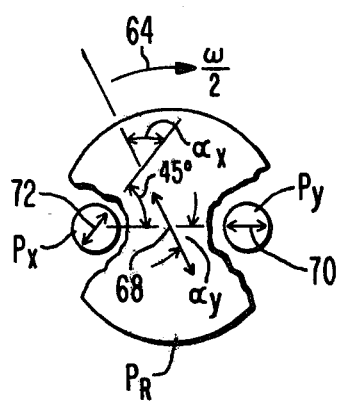
FIG. 4 is a plan view, partially fragmented of the polarizer and analyzers of FIG. 1, and FIGS. 5 and 6 are graphs of curves useful in illustrating the present invention.
Figure 5:
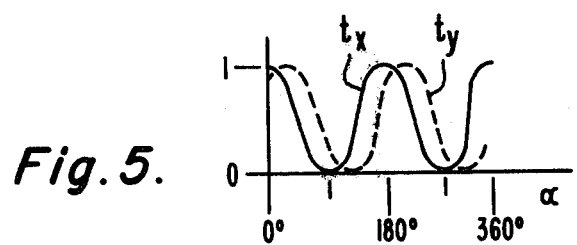

The transformation system 60 includes a rotating polarizer $P_R$ mounted to a rotating shaft 62 on table 42 for rotation in direction 64 (FIG. 4). A gear 66 connected to shaft 62 is meshed with gear 48 so that the polarizer $P_R$ rotates at an angular speed $\omega/2$ which is half the angular speed of the UUT. The polarizer $P_R$ is a thin sheet of polarizing material and has a given polarization orientation indicated by the arrow 68, FIG. 4. This orientation 68 rotates with the polarizer. Below the polarizer $P_R$ are a pair of spaced stationary analyzers $P_y$ and $P_x$. Analyzer $P_y$ has a polarization orientation 70 and the analyzer $P_x$ has a polarization orientation 72.

The polarization orientations of analyzers $P_y$ and $P_x$ are at 45° with respect to each other. For angular displacement of the UUT equal to zero, $\phi = 0$, the polarization orientation of polarizer $P_R$ is parallel to that of analyzer $P_y$.

If the angular displacement of the surface 14 of the UUT is given as $\phi$, and the angular displacement of the polarizer $P_R$ is $\alpha$, then $\alpha = -\phi/2$. It is known that the transmission t through a polarizer and analyzer is given by the expression $$t(\alpha) = \cos^2 \alpha \tag{1}$$

where $\alpha$ is the angle between the polarization direction of the polarizer and that of the analyzer. If we let the angle between the polarization direction of the analyzer $P_x$ and the polarizer $P_R$ be $\alpha_x$ then $$\alpha_x = -\phi/2 \tag{2}$$

substituting equation 2 into equation 1 gives $$t_x = \cos^2(-\phi/2) = \tfrac{1}{2}(1 + \cos \phi) \tag{3}$$

where $t_x$ is proportional to the transmission intensity of light passing through polarizer $P_R$ and analyzer $P_x$.

Since the polarization direction of analyzer $P_y$ is at 45° from that of analyzer $P_x$ then $$\alpha_y = \pi/4 - \phi/2 \tag{4}$$

where $\alpha_y$ is the angular displacement between the analyzer $P_y$ orientation 70 and the polarizer $P_R$ orientation 68. Substituting equation 4 into equation 1 gives $$t_y = \cos^2(\pi/4 - \phi/2) = \tfrac{1}{2}(1 + \cos(\pi/2 - \phi)) = \tfrac{1}{2}(1 + \sin \phi). \tag{5}$$

Thus it is seen that the transmission $t_y$ through the polarizer $P_R$ and analyzer $P_y$ is proportional to the sine of $\phi$ and the transmission $t_x$ through the polarizer $P_R$ and anayzer $P_x$ is proportional to the cosine of $\phi$, where $\phi$ is the angular displacement of the UUT from its reference orientation.

The source of the light discussed above is light emitting diodes $1_x$ and $1_y$ which are powered by power supply 73, FIG. 1. Diode $1_x$ is positioned above polarizer $P_R$ and analyzer $P_x$ while diode $1_y$ is positioned above polarizer $P_R$ and analyzer $P_y$. The light from the diodes $1_x$ and $1_y$ passes through the polarizer $P_R$ onto the respective analyzers $P_x$ and $P_y$. Photo detector 74 is positioned beneath analyzer $P_x$ and photo detector 76 is positioned beneath analyzer $P_y$ for detecting the respective transmissions $t_x$ and $t_y$ of the light from the diodes $1_x$ and $1_y$.

The transmitted signals from the detectors 74 and 76 are applied to the processing circuit 54. The detectors and the processing circuit 54 convert the light transmissions $t_x$ and $t_y$ into electrical signals proportional to the cosine and sine of $\phi$ and multiplies these signals by the signal R representing the linear displacement of the table 42 in the direction x. This produces an R sine $\phi$ signal which is applied to the y input of cathode-ray tube display 32 and an R cosine $\phi$ signal which is applied to the x input of cathode-ray tube display 32. This transformation is achieved by circuit 54 as follows.

Figure 2:
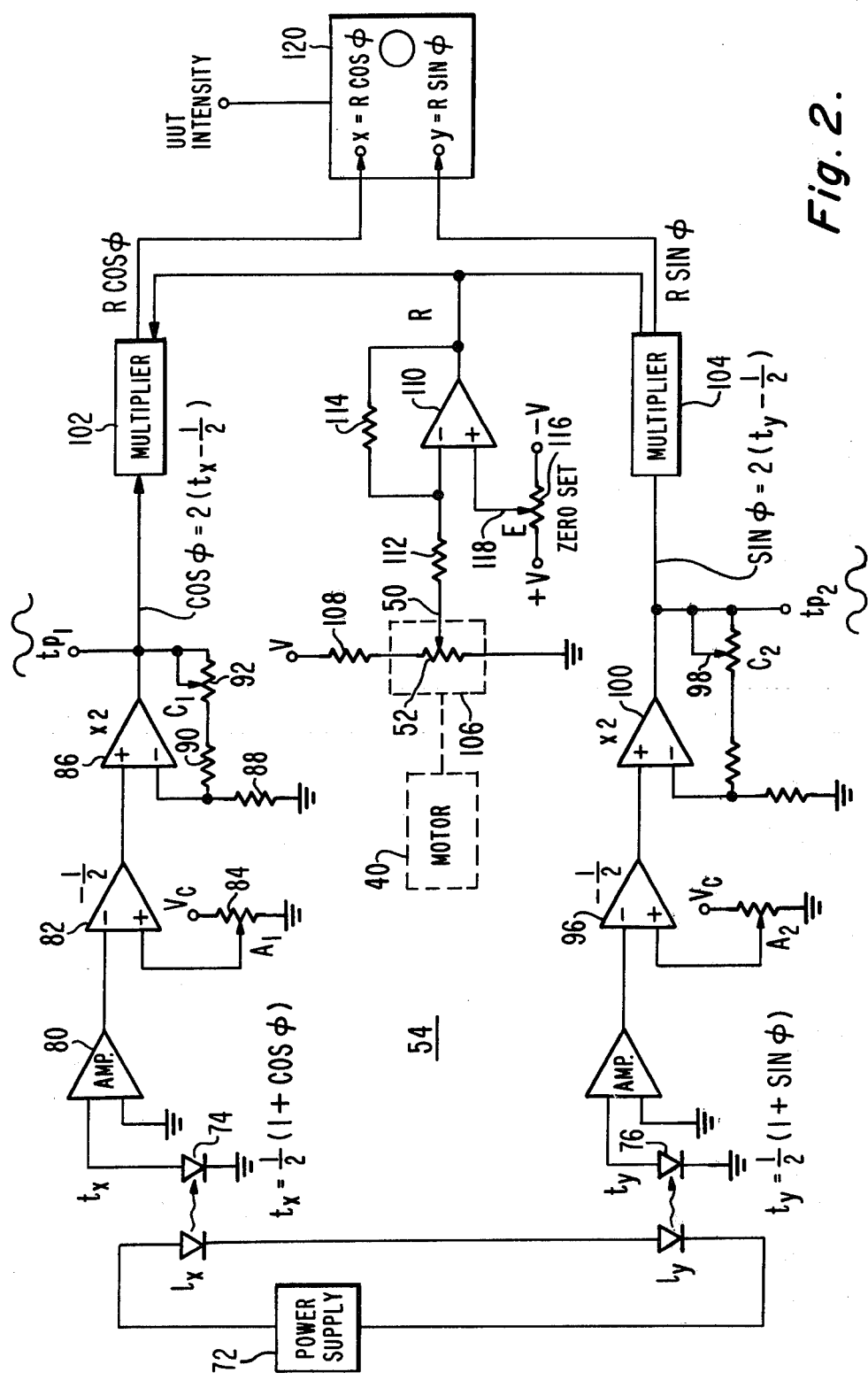
FIG. 2 is a circuit schematic diagram illustrating the processing circuit of FIG. 1.

Both the x and y channels include similar circuit components, therefore, only the x channel will be described. In FIG. 2, photo detector 74 detects the transmission intensity of the signal passed through the polarizer and analyzer for the x channel. The transmission $t_x$ is given by equation 3 and is proportional to the current in the photo detector 74 which is applied as an input to amplifier 80.

The output of amplifier 80 is applied to the inverting input of differential amplifier 82. The non-inverting input of amplifier 82 is connected to a variable resistance 84 connected between a source of voltage $V_C$ and ground. The potentiometer 84 provides an adjustment (designated $A_1$) to the signal representing $t_x$. This adjustment subtracts a constant from $t_x$ representing a value of approximately $\frac{1}{2}$. This gives a signal at the output of amplifier 82 corresponding to a value of $t_x - \frac{1}{2}$. This signal is applied to the non-inverting input of differential amplifier 86.

The inverting input of amplifier 86 is connected to ground through a resistor 88 and to the output of amplifier 86 through a fixed resistance 90 and a variable resistance 92. Variable resistance 92 permits adjustment of the feedback resistance of amplifier 86 to adjust the gain of amplifier 86. The gain is adjusted to provide a multiplication factor of approximately 2 to the output signal of amplifier 82. Therefore, the signal at the output of amplifier 86 will have a value corresponding to $2(t_x - \frac{1}{2})$.

Figure 6:
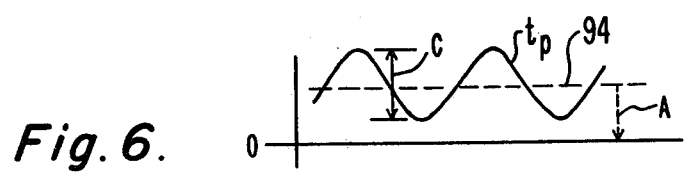

By referring to equation 3 it can be seen that the cosine $\phi$ expression represented by the output signal of amplifier 86 is a transformation of the expression of equation 3. The output of amplifier 86 is a signal which represents cosine $\phi$. The $A_1$ adjustment of potentiometer 84 as seen in FIG. 6 adjusts the DC level 94 of the waveform $t_p$ produced by amplifier 82 so that the DC level is approximately zero. The A adjustment is in the direction of the dashed arrow A of FIG. 6. In similar manner the $A_2$ adjustment of amplifier 96 in the y channel also sets the DC level of the output of amplifier 96 to zero.

Potentiometer 92 in the feedback path of amplifier 86 adjusts the peak-to-peak amplitude C of the waveform $t_p$. This forms the waveform $t_p$ into a good approximation of a sine wave. The A and C adjustments are made by observing the wave $t_p$ on an oscilloscope connected to test point $tp_1$, at the output of amplifier 86. In a similar manner, the potentiometer 98 of the y channel adjusts the peak-to-peak amplitude C of the y channel signal at the output of amplifier 100 as observed at test point $tp_2$. In this case, the output of amplifier 100 is a signal representing sine $\phi$.

The output of amplifier 86 is applied as an input to multiplier 102. The output of amplifier 100 in the y channel is applied as an input to multiplier 104.

The dashed box 106 represents the connection of wiper 50 to the table 42. Resistance 52 is connected to a source of voltage V through a resistance 108 at one end and to ground at the other end. Wiper 50 is connected to the inverting input of differential amplifier 110 through a resistance 112. Feedback resistance 114 has the same value as resistance 112 and is connected between the inverting input and the output of amplifier 110. Resistances 112 and 114 determine the gain of amplifier 110. Zero set potentiometer 116, which is connected between voltage sources $-V$ and $+V$, has its wiper 118 connected to the non-inverting input of amplifier 110. The output of amplifier 110 is applied as inputs to multipliers 102 and 104.

Figure 3:
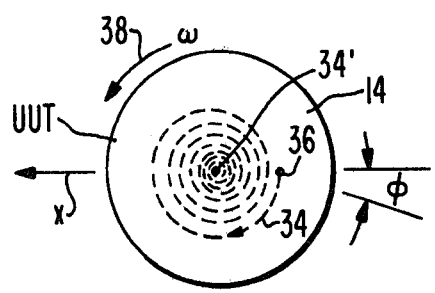
FIG. 3 is a plan view of the unit under test (UUT)

In operation, when the beam spot 36 is positioned at the center of the UUT along the axis of rotation 34' thereof, the output of amplifier 110 should be at zero. Because of the mechanical connections between the wiper 50 and the table 42, it is relatively difficult to zero adjust this amplifier by the wiper 50. Potentiometer 116 permits this zero adjustment easily to be made. The output signal of amplifier 110 is given as R, which represents the linear displacement of the spot 36 with respect to the axis of rotation of the UUT about shaft 38. Signal R is applied as one multiplying input to multipliers 102 and 104. Remembering that the other multiplying input to multiplier 102 is a signal representing cosine $\phi$ and the other input to multiplier 104 is a signal representing sine $\phi$, the outputs of multipliers 102 and 104 are respectively signals having an amplitude corresponding to R cosine $\phi$ and R sine $\phi$. These signals re applied to the respective x and y inputs of cathode-ray tube display 120 and cause the electron beam to scan the display screen along a spiral path corresponding to the spiral path of the spot of light over the surface of the UUT 14 as shown in FIG. 3. The unit under test (UUT) intensity signal $I_{UUT}$ produced by amplifier 28 is applied as an intensity input signal to the display 120 for intensity modulating the spirally scanned electron beam.

The display produced on display 120 is an area display with a dark background and with defects appearing as bright spots in positions on the screen corresponding to the spatial distribution of the locations of the defects on or close to the surface of the UUT 14.

As is now readily apparent, the 45° displacement of the analyzers $t_y$ and $t_x$ from each other provide the $\pi/4$ term in equation 5 above. Since equations 3 and 5 represent trigonometric functions in which the transmission intensities of the polarizers are transformed into sine and cosine terms, then it is readily apparent that the angular displacement of the polarization orientations of analyzers $P_x$ and $P_y$ is a function of that trigonometric function. Any other trigonometric expression which produces cosine and sine functions from the transmission intensities may be utilized to perform the transformation functions. These other expressions may provide angular orientations different than the 45° displacement between the x and y analyzers.

What is claimed is:

1. In a system for optically detecting microscopic defects in a certain specularly reflecting surface of a given object, said system comprising first means for scanning said surface with an incident beam of light that illuminates a relatively small spot area of said entire surface area, which spot area is large relative to the area of any microscopic defect, and second means for detecting substantially only non-specularly reflected light from said surface; the improvement:

wherein said first means includes third means for directing said incident beam substantially normal to said surface, whereby substantially all said specularly reflected light is reflected in a direction substantially normal to said surface, and wherein said second means includes a focusing device having a large aperture area relative to said spot area, said device being situated in spaced relationship with said spot area to subtend a certain solid angle disposed about a normal to said spot area, whereby substantially all reflected light within said certain solid angle may be captured by said device, and wherein said second means further includes a photo detector located in an image plane of said device for receiving light reflected by said surface, and a spatial filter having a small aperture area relative to that of said device situated between said device and said detector in the path of said received reflected light for removing that portion thereof which is specularly reflected.

2. The system defined in claim 1, wherein said spatial filter comprises a prism for deflecting that portion of said forwarded focused light incident thereon so that it does not reach said detector, said spatial filter being located relative to said focusing device so that substantially all said specularly reflected light after passing through said device, is incident on said prism.

3. The system defined in claim 2, wherein said focusing device includes a lens disposed with its principal plane substantially parallel to said specularly reflecting surface so that the optic axis of said lens is substantially perpendicular to said specularly reflecting surface, and wherein said prism is a 45°-45°-90° prism oriented with one side thereof substantially parallel to said optic axis of said lens and with the other side thereof substantially symmetrically disposed about said optic axis of said lens, whereby said specularly reflected light is totally reflected by said prism in a direction substantially normal to said optic axis of said lens.

4. The system defined in claim 3, wherein said first means includes a laser for generating a substantially plane wavefront beam of light and said third means directs said plane wavefront beam substantially normal to and incident on said prism, whereby said prism totally reflects said plane wavefront beam along said optic axis of said lens toward said specularly reflecting surface, whereby said totally reflected plane wavefront beam only passes through a central portion of said lens and is focused by said lens to said spot area of said specularly reflecting surface.

5. The system defined in claim 4, wherein said lens has an aperture in the order of one inch, said prism has an aperture in the order of one-quarter inch, and said spot area has a diameter in the order of two-hundred-fifty micrometers.

6. The system defined in claim 1, wherein said spot area has a diameter in the order of two-hundred-fifty micrometers, said device has an aperture in the order of one inch and said spatial filter has an aperture in the order of one-quarter inch.

7. The system of claim 1 wherein said first means includes scan means for scanning said certain surface area with said incident beam of light in a predetermined scan format, and wherein said system further includes a cathode-ray tube display, and signal translating means coupled to said scan means, said photo detector, and said cathode-ray tube display for displaying on said cathode-ray tube the spatial distribution of the locations of detected microscopic defects on said surface.

8. The system defined in claim 1 wherein said certain surface area is circular, wherein said predetermined scan format is a spiral scan format, and wherein said signal translating means includes processing means coupled between said scan means and said display to effect a spiral scan of the electron beam of the cathode-ray tube of said display in correspondence with the spiral scan of said certain surface with said incident beam of light, and intensity modulation means coupled between said photo detector and said display to effect intensity modulation of the electron beam of the cathode-ray tube of said display in accordance with the output of said photo detector.

9. An apparatus for scanning and displaying surface variations on an object comprising:
   means for projecting a beam of radiant energy parallel to a given axis normal to the surface, said surface variations tending to scatter energy reflected therefrom about said axis and for spatially filtering reflected energy from said surface,
   energy gathering means centered about said axis for gathering at least a portion of said scattered energy reflected about said axis,
   energy detecting means responsive to said gathered energy applied as an input thereto for producing an output signal proportional to the magnitude of the intensity of said gathered energy,
   scan means for scanning said beam over said surface and generating first and second scan signals representing the location of said beam on said surface, and
   means responsive to said output and scan signals for displaying said surface variations and their relative location on said surface.

10. The apparatus of claim 9 wherein said means for projecting includes a source of laser light and optic means for directing said light normal to said surface.

11. The apparatus of claim 9 wherein said gathering means includes light focusing means spaced from said surface, said focusing means focusing said beam as a spot of energy on said surface, said detecting means being spaced from said focusing means in the image plane of said focusing means, said focusing means focusing reflected energy from said spot onto said detecting means, said spot, focusing means and detecting means lying on a common axis.

12. The apparatus of claim 9 wherein said scan means includes polar to rectangular coordinate conversion means for moving a point on said object with respect to said beam in a spiral path and for generating said scan signals as x and y coordinate signals representing the location of said beam on said surface along said spiral path.

13. The apparatus of claim 9 wherein said scan means comprises:
   means for supporting said object,
   means for rotating said means for supporting,
   means for linearly displacing said means for supporting so that said beam follows a spiral path on said surface during said rotating,
   radiant energy polarizing means for generating said first and second scan signals representing the angular position of said beam on said surface,
   means for generating a displacement signal representing the linear displacement of said means for supporting, and
   circuit means for processing said displacement and first and second scan signals to produce third and fourth output signals representing the x and y coordinate positions of said beam on said path.

* * * * *